US00PP21613P3

(12) United States Plant Patent

Lowe et al.

(10) Patent No.: US PP21,613 P3

(45) Date of Patent: Jan. 11, 2011

(54) KIWI PLANT NAMED 'BRUCE'

(50) Latin Name: *Actinidia chinensis*
Varietal Denomination: Bruce

(75) Inventors: Russell G. Lowe, Te Puke (NZ); Bart Hofstee, Te Puke (NZ)

(73) Assignee: Zespri Group Limited, Mount Maunganui South (NZ)

( * ) Notice: Subject to any disclaimer, the term of this patent is extended or adjusted under 35 U.S.C. 154(b) by 59 days.

(21) Appl. No.: 12/380,453

(22) Filed: Feb. 26, 2009

(65) Prior Publication Data

US 2010/0011474 P1 Jan. 14, 2010

Related U.S. Application Data

(60) Provisional application No. 61/134,476, filed on Jul. 9, 2008.

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP11,066 P 9/1999 Lowe et al.

*Primary Examiner*—Susan B McCormick Ewoldt
(74) *Attorney, Agent, or Firm*—Knobbe, Martens, Olson & Bear LLP

(57) ABSTRACT

A new and distinct kiwifruit variety is described. The variety results from selection among a population of seedlings derived from a controlled pollination crossing the kiwifruit varieties known as 'Hort16A' (U.S. Plant Pat. No. 11,066) and an unreleased selection CK39_16 (not patented). The new variety is a male plant which flowers in a period well-synchronized for pollination of the female variety 'Hort16A' (U.S. Plant Pat. No. 11,066). The new variety is characterized by the timing of flowering, distinctive red/brown hairs evident on young shoots and the underside of young leaves. The new variety appears suitable for use as a pollinizer in commercial kiwifruit production and has been named 'Bruce'.

6 Drawing Sheets

Latin name of the genus and species of the plant claimed: *Actinidia chinensis.*

Variety denomination: 'Bruce'.

BACKGROUND AND SUMMARY OF THE INVENTION

Kiwi plants in cultivation are mainly varieties of *A. deliciosa,* particularly 'Hayward' although some *A. chinensis* and *A. arguta* varieties are grown. *A. deliciosa* and *A. chinensis* are closely related and varieties of both types have large fruit (~100 g) with hair on the skin. The main varieties in New Zealand are 'Hayward' (*A. deliciosa*) and 'Hort16A' (*A. chinensis*). Fruit are usually cut and eaten with a spoon.

All *Actinidia* species are dioecious, so female varieties have to be interplanted with male pollinizers to ensure fruit production.

*A. chinensis* vines are deciduous and tend to grow vigorously in spring and summer when rapidly-growing shoots can intertwine and tangle if not managed. Vines do best in a mild warm-temperate climate without late spring or early autumn frosts. They produce consistently heavy crops when grown in well-drained fertile soils and given regular irrigation in dry spells.

*A. chinensis* flowers in the spring (mid October-early December) in New Zealand. Harvest of *A. chinensis* fruit may occur between April and late-May in New Zealand depending on the selection and location of plantings.

Efficient pollination of female kiwifruit varieties influences seed numbers, which in turn influences fruit size and dry matter. In selecting new kiwifruit pollinizers the focus is on traits to enhance efficient pollination including pollen viability, pollen yield, number of flowers produced, and synchronization of the release of pollen from male flowers at the same time as the female flowers are receptive. A low vigor cultivar is preferred to minimize pruning costs.

The new variety was selected from a population of seedlings derived from a controlled pollination crossing of the kiwifruit varieties known as 'Hort16A' (U.S. Plant Pat. No. 11,066) and an unreleased selection CK39_16 (not patented) after observations of character and performance carried out from 1999 to 2000. The patented female parent 'Hort16A' was bred and selected in New Zealand, U.S. Plant Pat. No. 11,066. The unpatented male parent CK39_16 was selected in New Zealand from seedling plants raised from an introduction of open-pollinated seed from an un-patented parent from China in 1989. This new variety was created during the course of a planned plant-breeding program, which was initiated during 1995 in Te Puke, New Zealand. The cross was made on Oct. 29, 1995 in Te Puke, New Zealand. Seeds were sown in the spring of 1996 and 80 seedlings from this cross were planted out in the field at Te Puke in 1997. The selection 'Bruce' first flowered in October 2000. Selection 'Bruce' was grafted in 2000 onto five existing kiwifruit rootstocks at Te Puke, in a clonal selection trial plot, using graft wood from the original seedling plant.

The new variety was selected from among plants located on land at Te Puke, New Zealand, and was assigned the breeder code, 32-01-13a. The new variety has since been named 'Bruce'.

The present invention is a new and distinctive kiwifruit male variety whose flowering period coincides well with the patented female kiwifruit plant 'Hort16A' in most districts where kiwifruit are grown in New Zealand.

The new variety can be asexually reproduced as cuttings or by grafting or budding on to seedling or cutting-grown rootstocks of *A. deliciosa* or *A. chinensis*. Trial plantings of grafted plants established at Te Puke, Nelson and Kerikeri in 2003 have shown that the unique combination of characters come true to form and are established and transmitted through succeeding asexual propagations.

The new variety is characterized as follows:

Plant ploidy: Diploid.

Plant form and vigor: A twining habit, with strong vigor, similar to 'Hort16A' (U.S. Plant Pat. No. 11,066); the surface of the dormant cane is smooth and a white bloom is present; distinctive red/brown hairs are evident on the young shoots and the underside of young leaves.

Foliage: The mature leaf is broad ovate in shape; the upper surface of the leaf is smooth; the lobes of a mature leaf are arranged slightly overlapping.

Flower: The number of flowers in each inflorescence is typically between one to four flowers, with each inflorescence comprising a single king flower and one or two side flowers; the single colored petal is absent of any red blotch which is sometime present on the petals of flowers of other male varieties, for example 'Meteor' (not patented).

Time of flowering: Early.

Plant health: No visible leaf symptoms have been observed indicating the plant is not virus-infected. Resistance to pests and disease is unknown.

Pollination efficiency: The new variety was initially selected on the basis of its potential for synchrony of flowering with the commercially important New Zealand female kiwifruit variety 'Hort16A' (U.S. Plant Pat. No. 11,066) and the resulting large fruit size of fruit of 'Hort16A' (U.S. Plant Pat. No. 11,066) after hand pollination with excess pollen. Subsequent trials indicate that flowering of the new variety does appear to be well synchronized with when female flowers of the variety 'Hort16A' (U.S. Plant Pat. No. 11,066) are receptive in many production areas in New Zealand. Observations of the performance of the new variety indicate it has potential to bring about improved yield from 'Hort16A' (U.S. Plant Pat. No. 11,066) relative to other male pollinizers currently used commercially in New Zealand such as 'Meteor' (not patented) and 'Sparkler' (not patented) due to better coincidence with 'Hort16A' (U.S. Plant Pat. No. 11,066) flowering, and good ability to influence fruit size when pollen is delivered to the female flowers. Key attributes of the new variety in this regard include good pollen viability, and a high pollen yield, in combination with a medium flower load per plant (measured as the number of flowers per meter cane).

BRIEF DESCRIPTION OF THE DRAWINGS

The accompanying figures show typical specimens of the plant, foliage, and flowers of the new variety as depicted in colors as nearly true as is reasonably possible in a color representation of this type.

DETAILED BOTANICAL DESCRIPTION

Figure 1:
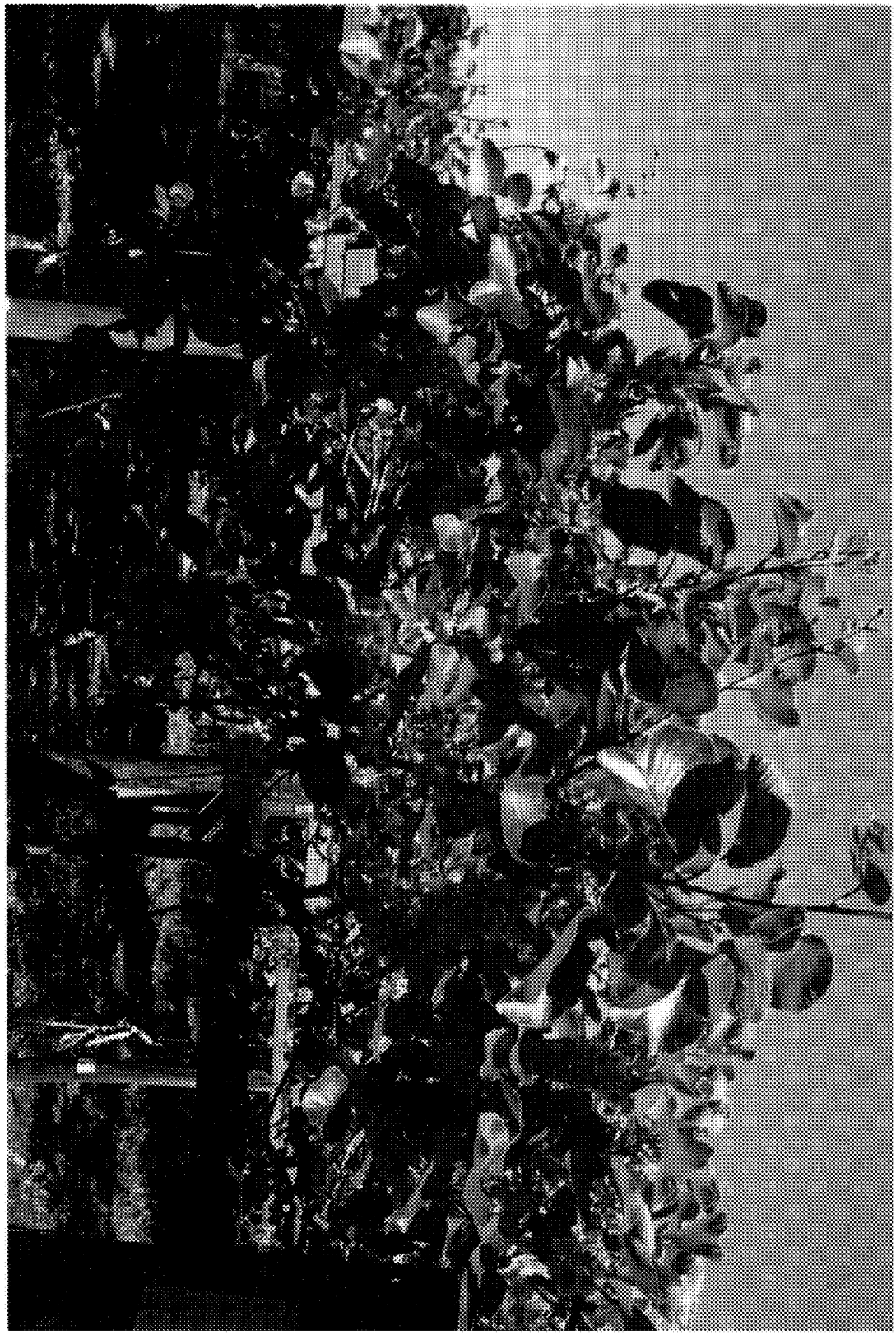
FIG. 1 shows a plant of the variety 'Bruce' in the field; view is of flower buds, open flowers, and new leaves.
Figure 2:
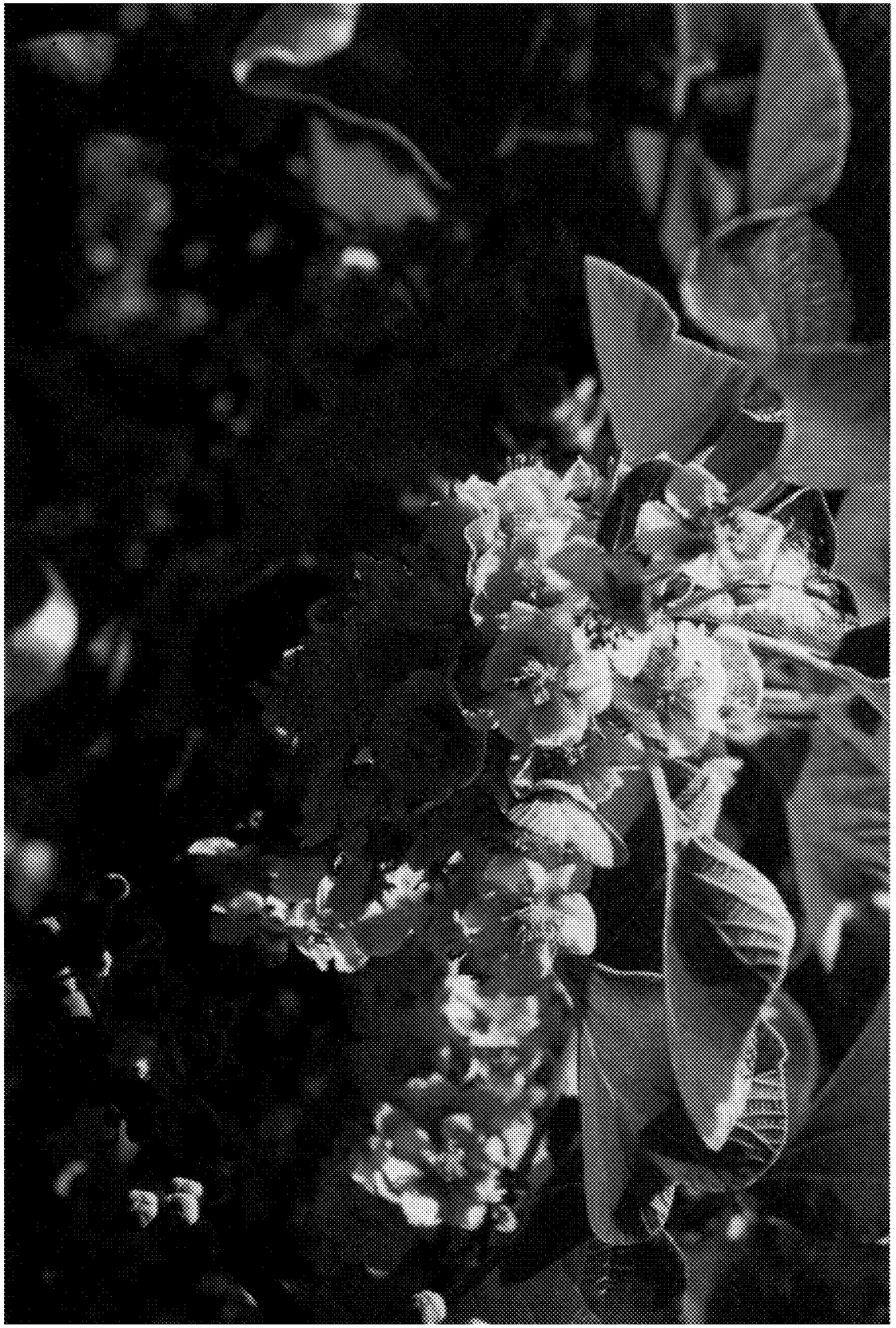
FIG. 2 shows an inflorescence of the variety 'Bruce'; view is of flower buds, open flowers, and pedicel.
Figure 3:
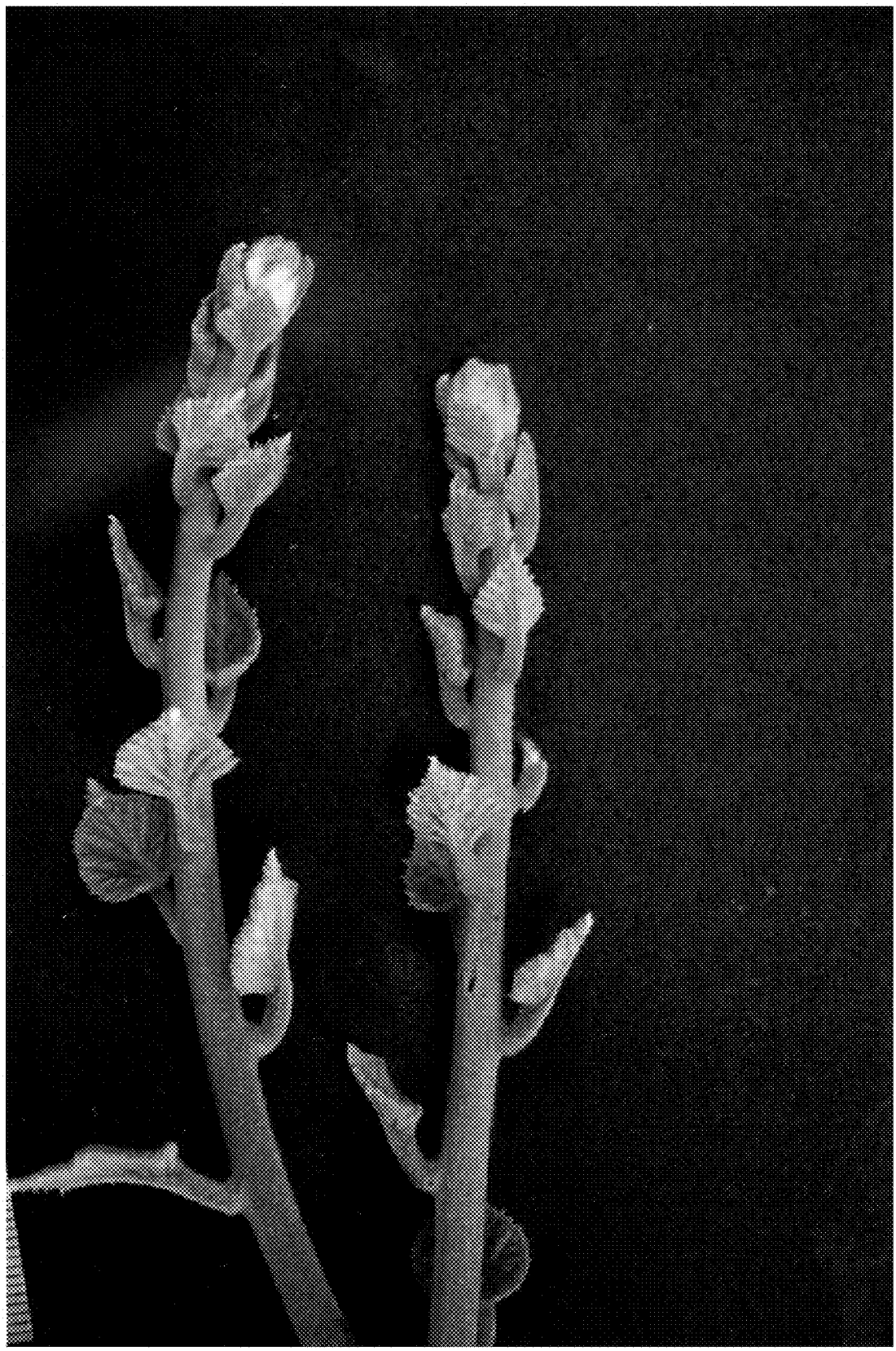
FIG. 3 shows the tip of a new shoot of the plant of the variety 'Bruce'; view shows the typical red coloration on the young shoot of 'Bruce'.
Figure 4:
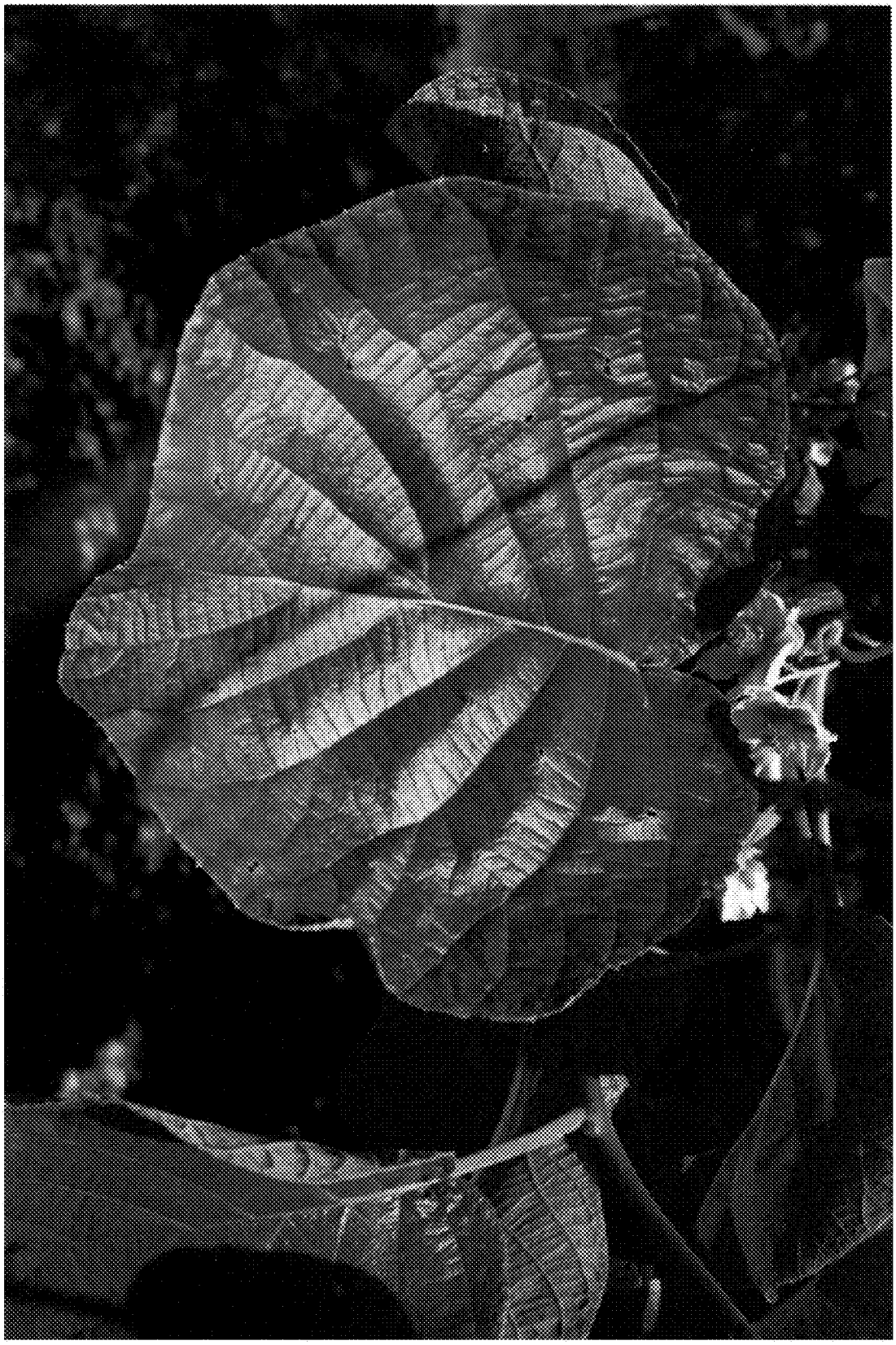
FIG. 4 shows a fully expanded leaf of the plant of the variety 'Bruce'.
Figure 5:
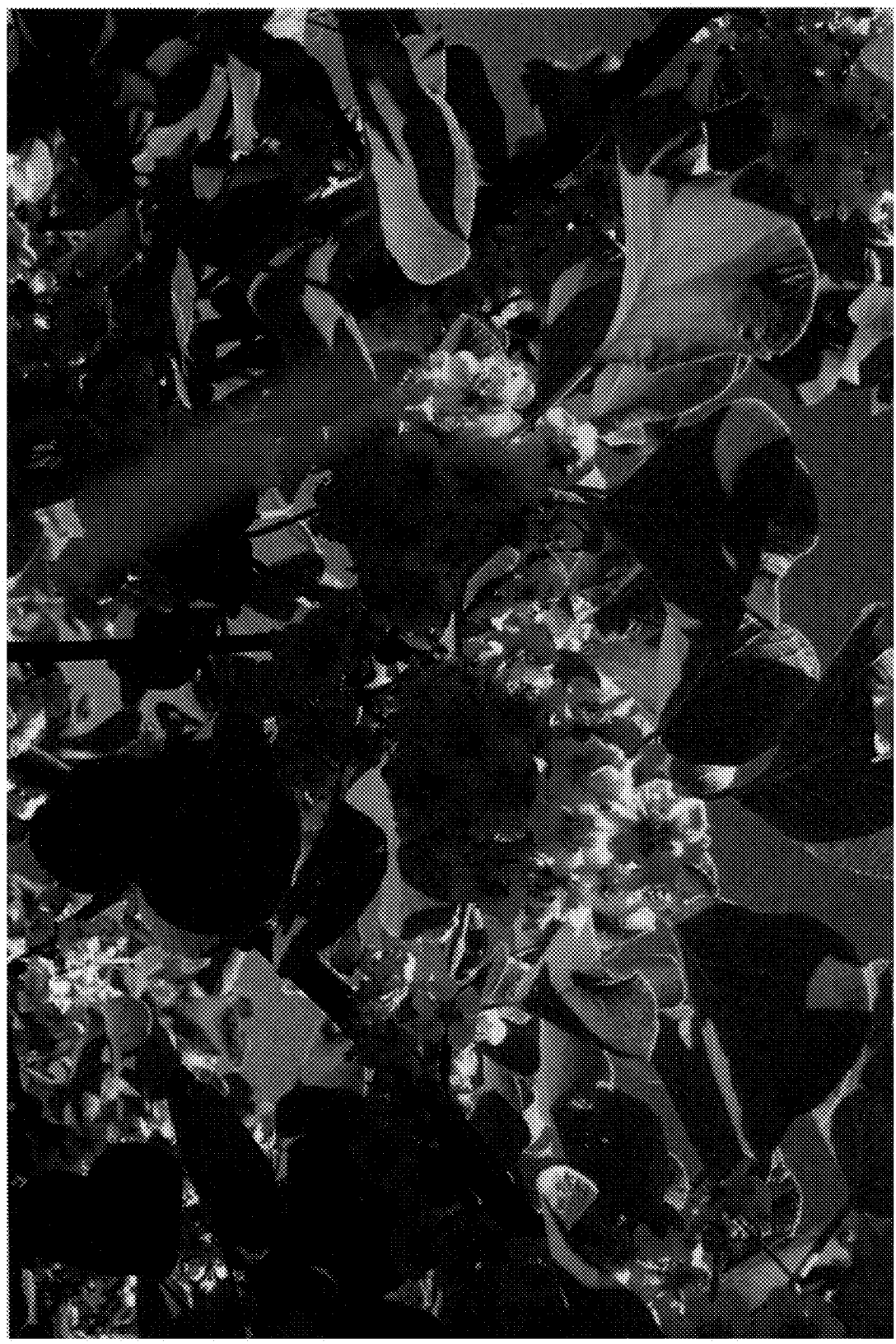
FIG. 5 shows a typical vine of the variety 'Bruce'.
Figure 6:
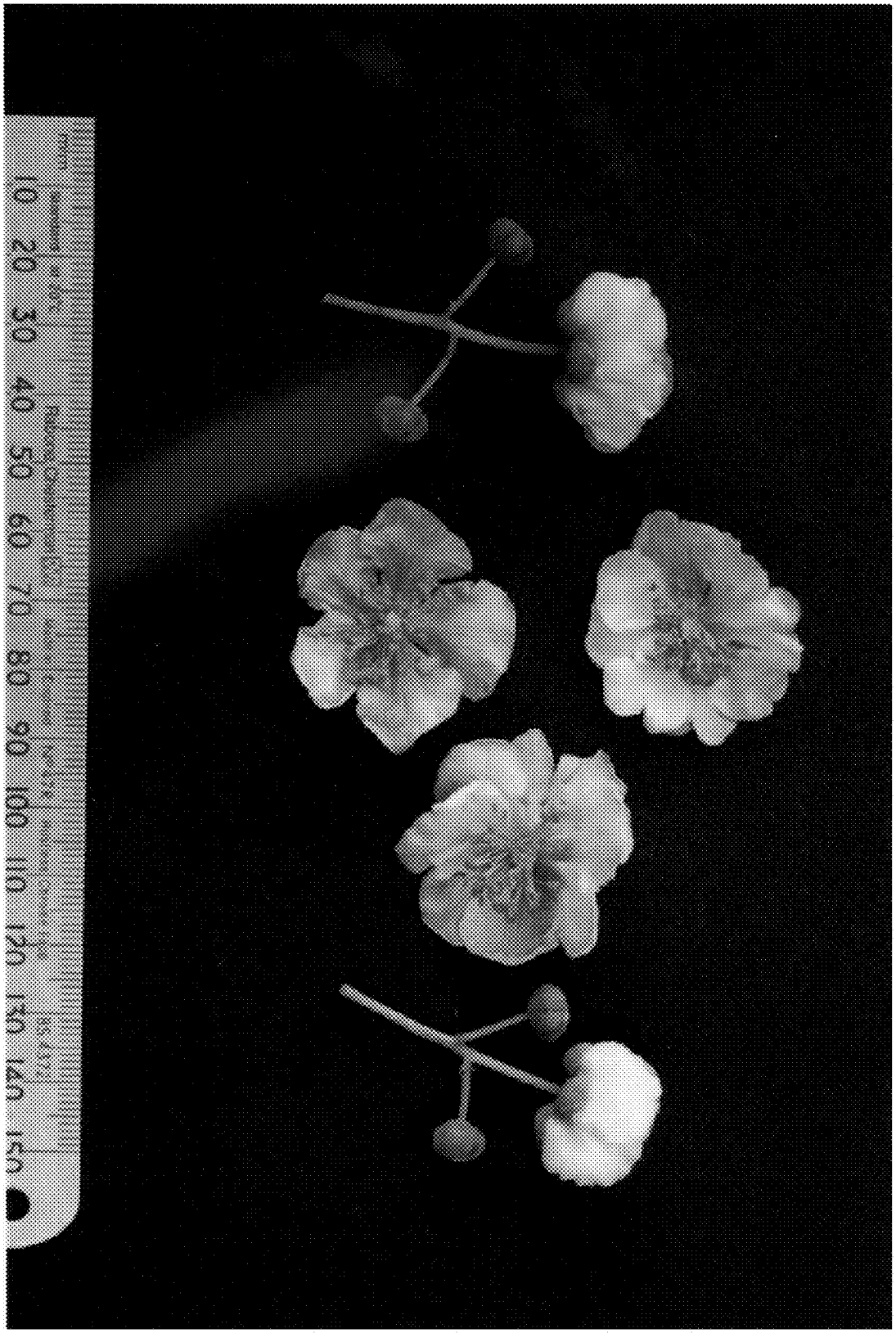
FIG. 6 shows typical flowers and buds of the variety 'Bruce'.

The following is a detailed description of the new variety. The new diploid kiwifruit variety 'Bruce' is staminate (male), produces only male flowers, and no fruit.

Horticultural terminology is used in accordance with UPOV guidelines for kiwi. All dimensions are in millimeters, and all weights are in grams (unless otherwise stated). Certain characteristics of this variety, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon The Royal Horticultural Society Colour Chart published by The Royal Horticultural Society, London, England.

TABLE 1

| CHARACTERISTICS | |
|---|---|
| | 'Bruce' |
| PLANT (Measurements from samples of 10, unless stated otherwise) | |
| Plant: sex expression | Male |
| Plant: ploidy | Diploid |
| Plant: vigour | Vigorous |
| Young shoot: hairs | Present |
| Young shoot: density of hairs | Dense |
| Young shoot: type of hairs | Tomentose |
| Young shoot: anthocyanin coloration of growing tip | Medium |
| Young shoot: anthocyanin coloration of leaf axil | Present |
| STEM | |
| Stem: coloration of leaf axil | Absent or very weak |
| Stem: diameter | Mean: 10.58 mm, Range: 8.7 mm-13.8 mm |
| Stem: length | Mean: 1.5 m, Range: 1.2-2.0 m |
| Stem: dormant bud diameter | Mean: 7.96 mm, Range: 6.9 mm-9.9 mm |
| Stem: color on upper side of dormant shoot | Grey-brown, R.H.S. 200C |
| Stem: character of bark | Smooth |
| Stem: hairs | Present |
| Stem: conspicuousness of lenticels | Conspicuous |
| Stem: number of lenticels/cm$^2$ bark | Mean: 4.0 lenticels, Range: 2.5-5.4 lenticels |
| Stem: color of lenticels | Orange-brown, R.H.S. 177C |
| Stem: size of lenticels-length | Mean: 2.34 mm, Range: 1.3 mm-3.5 mm |
| Stem: size of lenticels-maximum width | Mean: 1.67 mm, Range: 0.71 mm-2.08 mm |
| Stem: size of bud support | Mean: 4.9 mm, Range: 4.0 mm-5.9 mm |
| Stem: visibility of bud (dormant canes) | Visible |
| Stem: number of hairs visible on bud (dormant canes) | Many |
| Stem: presence of pith | Present |
| Stem: type of pith | Lamellate |

TABLE 1-continued

| CHARACTERISTICS | |
|---|---|
| | 'Bruce' |
| LEAF (Mature) | |
| Leaf: general shape of blade | Very broad ovate |
| Leaf: length | Mean: 144 mm, Range: 124 mm-164 mm |
| Leaf: width | Mean: 161 mm, Range: 138-185 mm |
| Leaf: petiole length | Mean: 158 mm, Range: 90-192 mm |
| Leaf: ratio leaf length to width | 0.90 |
| Leaf: ratio leaf length to petiole length | 0.91 |
| Leaf: shape of tip of blade | Acute |
| Leaf: shape of base of blade | Cordate |
| Leaf: arrangement of leaf bases | Slightly overlapping |
| Leaf: puckering/blistering on upper side of blade | Weak |
| Leaf: margin | Ciliate |
| Leaf: green color of upper side of blade | Medium green, R.H.S. 137A |
| Leaf: glossiness of upper surface of blade | Medium glossy |
| Leaf: color of lower side of blade | Light green, R.H.S. 137C |
| Leaf: glaucosity (lower side of blade) | Absent |
| Leaf: hairs on petiole | Present |
| Leaf: density of hairs on petiole | Dense |
| Leaf: anthocyanin coloration on upper side of petiole | Weak |
| FLOWER | |
| Inflorescence: predominant number of flowers | 3 |
| Flower: pedicel hairs | Present |
| Flower: pedicel, length of hairs | Very short |
| Flower: pedicel length | Mean: 36.7 mm, Range: 30.3 mm-45.2 mm |
| Flower: number of sepals | 5 to 7 |
| Flower: color of sepals | Yellow-green, R.H.S. 195A/147C |
| Flower: length of sepals | Mean: 6.23 mm, Range: 5.08 mm-7.65 mm |
| Flower: diameter of sepals | Mean: 4.65 mm, Range: 3.69 mm-6.01 mm |
| Flower: diameter (terminal or king flower when fully open) | Mean: 36.2 mm, Range: 25.3 mm-40.7 mm |
| Flower: mean number of petals per flower | Mean: 6.8 petals, Range: 5-9 petals |
| Flower: length of petals | Mean: 16.43 mm, Range: 14.5 mm-18.0 mm |
| Flower: width of petals | Mean: 15.24 mm, Range: 12.8 mm-18.1 mm |
| Flower: ratio petal length/width | 1.15 |
| Flower: arrangement of petals | Overlapping |
| Flower: petal curvature of apex | Strongly expressed |
| Flower: primary color of petals (when fully open) | White, R.H.S. 158D |
| Flower: type of coloration of petals | Bi-color |
| Flower: secondary color of base of petals. | Green, R.H.S. 146D |
| Flower: filament color | Greenish-white, R.H.S. 157A |
| Flower: anther color | Yellow/orange, R.H.S. 163A |
| Flower. anther number per flower | Mean. 52.2 anthers, Range: 37-68 anthers |
| EVENTS | |
| Time of vegetative budbreak | Early-similar to Hort16A female |
| Time of beginning of flowering | Early-similar to Hort16A female |

Observations were made on plants grown at Te Puke, New Zealand. These plants had been grafted on to seedling kiwifruit rootstocks.

Rootstocks

'Bruce' vines can be grown on the same rootstocks as can 'Hort16A'. Rootstocks currently being used in New Zealand include *A. deliciosa* and *A. chinensis* seedlings, 'Hayward' (not patented) and 'Kaimai' (not patented) rooted cuttings.

Flowering and Plant Management

Young vines of 'Bruce' flower heavily when young, and most flowers should be removed from grafts and young plants to allow the plant to establish a good canopy of canes. Mature plants can be pruned after flowering by removing up to two thirds of the canopy and allowing new canes to establish over the growing period. Minimal pruning is done in winter.

Pest and Disease Resistance/Susceptibility

Pest and disease issues are of minor significance for non-cropping pollinizers, and at this stage we have not recorded any particular susceptibilities to pests or diseases for this male variety.

Comparison to Closest Cultivar

The distinctive characteristics of this new kiwifruit variety, described in detail below, were observed in 2007 at Te Puke, New Zealand. The age of the plants was 7 years from grafting onto seedling rootstocks.

Comparison with similar male varieties, 'Meteor' and 'Sparkler', in commercial use in New Zealand shows that 'Bruce' can be distinguished from these varieties as outlined in Table 1.

TABLE 2

| COMPARISON WITH SIMILAR VARIETIES | | | |
|---|---|---|---|
| Characteristic | Bruce | Meteor | Sparkler |
| Flower: Petal color blotch presence | Absent | Present | Absent |
| Surface of dormant cane | Smooth | Rough | Smooth |
| Color of hairs on young shoots and leaves | Red/Brown | Pale Brown | Pale red |
| White bloom on dormant cane | Present, medium expression | Not present or weak | Present, strong expression |
| Upper surface of leaf to the touch | Smooth | Rough | Smooth |
| Mature leaf lobe arrangement | Slightly overlapping | Overlapping | Touching |
| Time of flowering in relation to 'Hort16A' female | Starts at same time as 'Hort16A' | Starts up to 10 days before 'Hort16A' | Starts from 2-7 days after 'Hort16A' |

'Meteor' and 'Bruce' are relatively easy to distinguish in that 'Meteor' has a rough surface of canes and upper surface of leaves, has a pink blotch on petals at time of flowering and weak expression of white bloom on dormant canes, whereas 'Bruce' has smooth leaves and canes, no pink blotch on flowers and medium expression of white bloom on dormant canes. 'Sparkler' and 'Bruce' are more similar in appearance overall as both have smooth leaves and canes, but 'Sparkler' commences flowering up to 7 days later than 'Bruce' and the young flowering shoots of 'Bruce' and the undersides of young leaves have a much more intense red color compared to 'Sparkler'. In addition, 'Bruce' leaf lobes are slightly overlapping, while 'Sparkler' leaf lobes are touching.

We claim:

1. A new and distinct kiwi plant as herein described and illustrated, selected from seedlings derived from a controlled pollination crossing of the kiwifruit varieties known as 'Hort16A' (U.S. Plant Pat. No. 11,066) and an unreleased selection CK39_16 (not patented) and characterized by its appearance and flowering period.

* * * * *